United States Patent

Suami et al.

[11] 4,086,415
[45] Apr. 25, 1978

[54] NITROSOUREA DERIVATIVES OF GLYCOSIDES

[75] Inventors: Tetsuo Suami, No. 5-8, 3-chome, Nakamachi, Musashino-shi, Tokyo, Japan; Tomoya Machinami, Shiraoka; Takashi Hisamatsu, Yokohama, both of Japan

[73] Assignee: Tetsuo Suami, Musashino, Japan

[21] Appl. No.: 600,206

[22] Filed: Jul. 30, 1975

[30] Foreign Application Priority Data

Aug. 8, 1974    Japan ................................. 49-90266

[51] Int. Cl.$^2$ ............................................. C07H 11/02
[52] U.S. Cl. ......................................... 536/22; 536/4;
536/17; 536/18; 536/53; 424/180
[58] Field of Search ........ 260/210 R, 211 R, 211.5 R;
536/18, 22, 53, 4

[56] References Cited

U.S. PATENT DOCUMENTS

| | | | |
|---|---|---|---|
| 3,577,406 | 5/1971 | Hessler | 260/211 R |
| 3,694,428 | 9/1972 | Hardegger et al. | 260/211 R |
| 3,767,640 | 10/1973 | Suami et al. | 260/210 R |

*Primary Examiner*—Johnnie R. Brown
*Attorney, Agent, or Firm*—Larson, Taylor and Hinds

[57] ABSTRACT

New nitrosourea derivatives are provided, which possess a high inhibitory activity against the leukemia and tumors with a low toxicity and which are useful for pharmaceutical purposes. The compounds have the formula

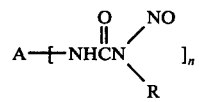

wherein A represents a glycosyl group, a monovalent residue of methyl glucoside or of alditol, a N-substituted carbamoyloxyalkyl group or a hydroxy-substituted cyclohexyl group when $n$ is 1, or A represents a tetravalent residue of ribostamycin when $n$ is 4 and R represents a lower alkyl or halo-alkyl group and are prepared by treating a compound of the formula

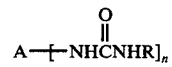

with a nitrosating agent.

7 Claims, No Drawings

NITROSOUREA DERIVATIVES OF GLYCOSIDES

This invention relates to new nitrosourea derivatives which exhibit a high activity against the leukemia and tumors with a low toxicity and which are therefore useful in the therapeutic treatment of the leukemia and tumors. This invention also relates to a process for the preparation of such new nitrosourea derivatives and to their use for pharmaceutical purposes.

There have already been proposed and known many chemicals which exhibit an inhibitory activity against the leukemia and tumors, but which are not satisfactory in the level of activity and/or toxicity.

We have now found that certain new nitrosourea derivatives, as hereinafter defined, possess a significantly high inhibitory activity against the leukemia and tumors with a low toxicity as evidenced, for example, by in vivo tests.

According to one aspect of this invention, therefore, there are provided as new compounds nitrosourea derivatives of the formula:

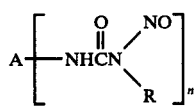 (I)

wherein A represents a glycosyl group, a monovalent residue of methyl glucoside from which the 2-hydroxy group has been removed, a monovalent residue of alditol from which the 2-hydroxy group has been removed, N-substituted carbamoyloxyalkyl group or a hydroxy-substituted cyclohexyl group when n is 1, or A represents a tetravalent residue of ribostamycin from which the four amino groups have been removed when n is 4 and R represents a lower alkyl group or a halo-substituted lower alkyl group, provided that R is not methyl group when A is glucosyl group.

When A represents a glycosyl group, it may be those not only derived from monose but also from biose and may be in the form of a deoxy derivative. Similarly, when A represents a monovalent residue of methyl glucoside, it may be in the form of a deoxy derivative.

Of the new nitrosourea derivatives of the formula I according to this invention, the first group of preferred compounds is represented by the formula Ia:

 (Ia)

wherein $A^1$ represents β-D-glucopyranosyl group and $R^1$ represents an alkyl group having 2-4 carbon atoms or a halo-substituted alkyl group having 1-4 carbon atoms.

Typical examples of the compounds of the formula Ia include:

1-ethyl-3-(β-D-glucopyranosyl)-1-nitrosourea;
1-(β-D-glucopyranosyl)-3-nitroso-3-n-propylurea;
1-n-butyl-3-(β-D-glucopyranosyl)-1-nitrosourea; and
1-(2-chloroethyl)-3-(β-D-glucopyranosyl)-1-nitrosourea.

The second group of preferred compounds of the formula I is represented by the formula Ib:

 (Ib)

wherein $A^2$ represents mannopyranosyl group or galactopyranosyl group and $R_2$ represents an alkyl group having 1-4 carbon atoms or a halo-substituted alkyl group having 1-4 carbon atoms.

Typical examples of the compunds of the formula Ib include:

1-(2-chloroethyl)-3-(β-D-mannopyranosyl)-1-nitrosourea; and
1-(2-chloroethyl)-3-(β-D-galactopyranosyl)-1-nitrosourea.

The third group of preferred compounds of the formula I is represented by the formula Ic:

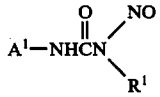 (Ic)

wherein $A^3$ represents a glycosyl group or a hydroxyl-substituted cyclohexyl group and $R^2$ represents an alkyl group having 1-4 carbon atoms or a halo-substituted alkyl group having 1-4 carbon atoms.

In the compounds of the formula Ic, the glycosyl group may be, for example, arabinosyl, xylosyl, lyxosyl, talosyl, idosyl, gulosyl, altrosyl or allosyl group and the hydroxy-substituted cyclohexyl group may be, for example, a mono-hydroxycyclohexyl group such as 2-, 3- or 4-hydroxycyclohexyl group, a di-hydroxycyclohexyl group such as 2,3-, 2,4-, 2,5-, 2,6-, 3,4-, or 3,5-dihydroxycyclohexyl) group, a tri-hydroxycyclohexyl group such as 2,3,4-, 2,3,5-, 2,3,6-, 3,4,5-, or 3,4,6-trihydroxycyclohexyl group or a tetra-hydroxycyclohexyl group such as 2,3,4,5-, 2,3,4,6-, or 2,3,5,6-tetrahydroxycyclohexyl group.

Typical examples of the compounds of the formula Ic include:

1-methyl-1-nitroso-3-(β-D-xylopyranosyl)urea;
1-(2-chloroethyl)-1-nitroso-3-(β-D-xylopyranosyl)urea;
1-(1,3/2N-dihydroxycyclohexyl)-3-methyl-3-nitrosourea; and
1-(2-chloroethyl)-3-(1,3/2N-dihydroxycyclohexyl)-1-nitrosourea.

The fourth group of preferred compounds of the formula I is represented by the formula Id:

 (Id)

wherein $A^4$ represents mannopyranosyl group, methyl 2,6-dideoxy-glucopyranoside residue of the formula:

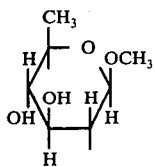

or methyl 2-deoxy-6O-mesyl-β-D-glucopyranoside residue of the formula:

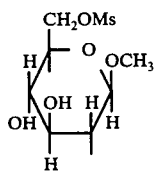

wherein Ms represents mesyl group.

Typical examples of the compounds of the formula Id include:

1-(β-D-mannopyranosyl)-3-methyl-3-nitrosourea;
methyl 2,6-dideoxy-2-(N'-methyl-N'-nitrosoureido)-β-D-glucopyranoside; and
methyl 2-deoxy-6-O-mesyl-2-(N'-methyl-N'-nitrosoureido)-β-D-glucopyranoside.

The fifth group of preferred compounds of the formula I is represented by the formula Ie:

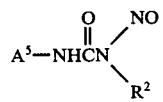

wherein $A^5$ represents pentahydroxy-cyclohexyl group and $R^2$ represents an alkyl group having 1–4 carbon atoms or a halo-substituted alkyl group having 1–4 carbon atoms.

Typical example of the compounds of the formula Ie includes;

1-(2-chloroethyl)-1-nitroso-3-(1N,3,5/2,4,6-pentahydroxy-cyclohexyl)urea.

The sixth group of preferred compounds of the formula I is represented by the formula If:

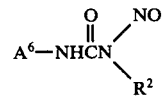

wherein $A^6$ represents a glycosyl group derived from biose and $R^2$ represents an alkyl group having 1–4 carbon atoms or a halo-substituted alkyl group having 1–4 carbon atoms.

As glycosyl group derived from biose there may be mentioned maltosyl, lactosyl, sucrosyl, cellobiosyl, trehalosyl, gentiobiosyl, melibiosyl, turanosyl, sophorosyl or isosucrosyl group.

Typical examples of the compounds of the formula If include:

1-(β-D-maltosyl)-3-methyl-3-nitrosourea;
1-(2-chloroethyl)-3-(β-D-maltosyl)-1-nitrosourea;
1-(β-D-lactosyl)-3-methyl-3-nitrosourea; and
1-(2-chloroethyl)-3-(β-D-lactosyl)-1-nitrosourea.

The seventh group of preferred compounds of the formula I is represented by the formula Ig:

wherein $A^7$ represents a monovalent residue of alditol from which the 2-hydroxy group has been removed which has the formula:

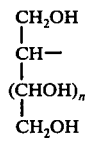

where $n$ represents O or an integer of 1–3 and $R_2$ represents a halo-substituted alkyl group having 1–4 carbon atoms.

The monovalent residue of alditol as $A^7$ may be any of those derived from tritol, tetritol, pentitol and hexitol.

Typical examples of the compounds of the formula Ig include:

N-carbamoyl-N'-(2-chloroethyl)-N'-nitroso-D-glucosaminol; and
N-carbamoyl-N'-(2-chloroethyl)-N'-nitroso-D-galactosaminol.

The eighth group of preferred compounds of the formula I is represented by the formula Ih:

wherein $A^8$ represents a N-substituted carbamoyloxyalkyl group of the formula:

wherein $R^3$ represents an alkylene group having 2–5 carbon atoms and $R^4$ represents an alkyl group having 1–4 carbon atoms or a halo-substituted alkyl group having 1–4 carbon atoms and $R^2$ represents an alkyl group having 1–4 carbon atoms or a halo-substituted alkyl group having 1–4 carbon atoms.

As the alkylene group $R^3$, there may be mentioned ethylene, trimethylene, propylene, tetramethylene, 1,2-dimethylethylene, pentamethylene, 1-methyltetramethylene, 2-methyltetramethylene, 1,2-dimethyltrimethylene and 1,3-dimethyltrimethylene groups.

Typical examples of the compounds of the formula Ih include:

(N-carbamoyl-N'-methyl-N'-nitroso)-(O-carbamoylmethyl)-ethanolamine; and
[N-carbamoyl-N'-(2-chloroethyl)-N'-nitroso]-(O-carbamoyl-N'-2-chloroethyl)-ethanolamine.

The ninth group of preferred compounds of the formula I is represented by the formula Ii:

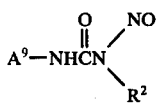

wherein $A^9$ represents 6-deoxy-glucopyranosyl group and $R^2$ represents an alkyl group having 1–4 carbon atoms or a halo-substituted alkyl group having 1–4 carbon atoms.

Typical examples of the compounds of the formula Ii include:

1-(6-deoxy-β-D-glucopyranosyl)-3-methyl-3-nitrosourea; and
1-(2-chloroethyl)-3-(6-deoxy-β-D-glucopyranosyl)-1-nitrosourea.

The tenth group of preferred compounds of the formula I is represented by the formula Ij:

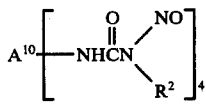

wherein $A^{10}$ represents a tetravalent residue of ribostamycin having the formula:

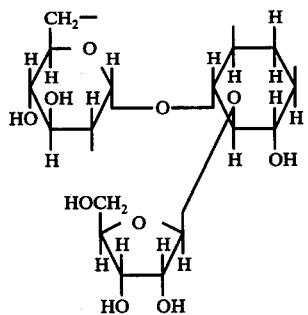

and $R^2$ represents an alkyl group having 1–4 carbon atoms or a halo-substituted alkyl group having 1–4 carbon atoms.

Typical examples of the compounds of the formula Ij include:

tetra-N-(N'-methyl-N'-nitroso)carbamoyl-ribostamycin; and
tetra-N-[N'-(2-chloroethyl)-N'-nitroso] carbamoyl-ribostamycin.

The new nitrosourea derivatives of the formula I according to this invention have been shown to exhibit a high inhibitory activity to the leukemia and tumors with a low toxicity.

According to another aspect of this invention, therefore, there is provided a pharmaceutical composition comprising a nitrosourea derivative of the formula I in association with a pharmaceutical carrier or diluent.

The pharmaceutical composition may be in some pharamaceutical form known in the art. Thus, the nature of the composition and the pharmaceutical carrier or diluent will, of course, be dependent upon the route of administration, e.g. orally or parenterally. In general, the composition may be in a form suitable for injection or oral administration such as in the form of ampoule, capsule, tablet, powder, granule and others.

This invention also includes within its scope a method for the therapeutic treatment of leukemic and tumor diseases in animals which comprises administering to the animals a therapeutically effective amount, at suitable intervals, of a nitrosourea derivative of the formula I above. It will be appreciated that the actually applied amount of the nitrosourea derivatives used will vary dependent upon the particular compound used, the particular composition formulated, the mode of application, the route of administration and others. Many factors which modify the action of the drug will be taken into account by the skilled in the art, for example, age, body weight, sex, diet, time of administration, route of administration, rate of metabolism or excretion, drug combination, sensitivities and severity or condition of the disease. Optimal application dose for a given set of conditions can be ascertained by the skilled in the art using conventional tests for the dosage determination in view of the above guidelines.

Chemotherapeutic effect of a variety of the nitrosourea derivatives of the formula I according to this invention on leukemia L1210 in mice were investigated by the following method and materials.

| Compounds tested | |
|---|---|
| Compound No. | Name |
| 1 | 1-(2-chloroethyl)-3-(β-D-glucopyranosyl)-1-nitrosourea |
| 2 | 1-(2-chloroethyl)-3-(β-D-mannopyranosyl)-1-nitrosourea |
| 3 | 1-(2-chloroethyl)-1-nitroso-3-(β-D-xylopyranosyl)urea |
| 4 | 1-(2-chloroethyl)-3-(1,3/2N-dihydroxycyclohexyl)-1-nitrosourea |
| 5 | 1-(2-chloroethyl)-1-nitroso-3-(1N,3,5/2,4,6-pentahydroxycyclohexyl)urea |
| 6 | Methyl 2,6-dideoxy-2-(N'-methyl-N'-nitrosoureido)β-D-glucopyranoside |
| 7 | 1-(2-chloroethyl)-3-(β-D-galactopyranosyl)-1-nitrosourea |
| 8 | 1-(2-chloroethyl)-3-(β-D-lactosyl)-1-nitrosourea |
| 9 | N-carbamoyl-N'-(2-chloroethyl)-N'-nitroso-D-glucosaminol |
| 10 | Daunomycin (Reference 1) |
| 11 | 1-(β-D-glucopyranosyl)-3-methyl-3-nitrosourea (Reference 2) |
| 12 | N-carbamoyl-N'-methyl-N'-nitroso-D-glucosaminol (Reference 3) |
| Animals used for the tests | |
| A | $BDF_1$ mice (about 6 week-aged; body weight: 22 ±1 g); each experimental group was composed of 2 male mice. |
| B | $BDF_1$ mice (about 7 week-aged; body weight: 21 ±2 g); each experimental group was composed of 3 male mice. |
| C | BDF mice (about 7 week-aged; body weight; 22 ±2 g); each experimental group was composed of 2 male mice. |
| D | BDF mice (about 6 week-aged; body weight: 21 ±2 g); each experimental group was composed of 3 male mice. |
| E | $BDF_1$ mice (about six week-aged; body weight 20 ±1 g); each experimental group was composed of 3 female mice. |
| F | $BDF_1$ mice (about six week-aged; body weight 21 ±1 g); each experimental group was composed of 3 male mice. |
| Tumor cells inoculated for the tests | |
| A | Leukemia L1210 cells (2.1 × $10^6$ cells/0.05 ml/mouse) were intraperitoneally inoculated. |
| B | Leukemia L1210 cells (1.9 × $10^6$ cells/0.05 ml/mouse) were intraperitoneally inoculated |
| C | Leukemia L1210 cells (1.2 × $10^6$ cells/0.05 ml/mouse) were intraperitoneally |

-continued

Test procedures

A  The test compound was dissolved in a physiological saline solution and administered intraperitoneally at a volume of 0.1 ml/mouse. The administration was made at once/day, from 24 hours after i.p. inoculation of L1210 cells, for 3 days. The effect of test compound was assessed by mean survival days of mice, percent increase in life-span, anatomical findings involving the volume of ascites.

B  The same as that used in A except that the drug administration was continued for 5 days.

C  The same as that used in A except that the test compound was suspended in 0.5% CMC solution and that the drug administration was continued for 5 days.

D  The same as that used in A except that the test compound was dissolved in distilled water for injection purposes.

The results of tests are summarized in Table 1. The percentage increases in life-span (ILS) was calculated as follows:

$$\text{Percentage increase in life-span (ILS)} = \frac{T - C}{C} \times 100$$

T: The mean survival days of the treated animals.
C: The mean survival days of the untreated control.

Table 1

| Compound No. | Animals | Tumor | Test procedure | Dose mg/kg | Survival days Treated/Control | ILS % | Volume of ascites Treated/Control |
|---|---|---|---|---|---|---|---|
| 1 | A | A | A | 10 | 95.9/9.3 | 931.1 | 0/4.7 |
|   |   |   |   | 8 | 95.9/9.3 | 931.1 | 0/4.7 |
|   |   |   |   | 6.25 | >40.1/9.3 | >331.2 | 0/4.7 |
|   |   |   |   | 5 | 15.3/9.3 | 64.5 | 1.5/4.7 |
|   |   |   |   | 4 | 40.3/9.3 | 333.3 | 0/4.7 |
|   |   |   |   | 2 | 15.3/9.3 | 64.5 | 2.5/4.7 |
|   |   |   |   | 1 | 12.9/9.3 | 38.7 | 5.0/4.7 |
|   |   |   |   | 0.5 | 12.5/9.3 | 34.4 | 4.2/4.7 |
|   |   |   |   | 0.2 | 12.0/9.3 | 29.0 | 4.2/4.7 |
| 2 | D | A | A | 8 | 18.3/9 | 103.3 | 0/2.8 |
|   |   |   |   | 4 | 15.0/9 | 66.7 | 1.2/2.8 |
|   |   |   |   | 2 | 14.7/9 | 63.0 | 1.2/2.8 |
|   |   |   |   | 1 | 13.7/9 | 51.9 | 2.3/2.8 |
|   |   |   |   | 0.5 | 13.0/9 | 44.4 | 3.0/2.8 |
| 3 | D | A | A | 16 | 9.0/11.0 | −18.2 | 0/3.0 |
|   |   |   |   | 8 | >60.0/11.0 | >445.5 | 0/3.0 |
|   |   |   |   | 4 | >60.0/11.0 | >445.5 | 0/3.0 |
|   |   |   |   | 2 | >24.0/11.0 | >118.2 | 0/3.0 |
|   |   |   |   | 1 | 17.0/11.0 | 54.5 | 0/3.0 |
| 4 | B | B | A | 16 | 13.0/10.3 | 26.2 | 0/2.7 |
|   |   |   |   | 8 | >59.3/10.3 | >475.7 | 0/2.7 |
|   |   |   |   | 4 | >60.0/10.3 | >482.5 | 0/2.7 |
|   |   |   |   | 2 | 22.0/10.3 | 113.6 | 0.8/2.7 |
| 5 | A | A | A | 30 | 11.6/9.7 | 19.6 | 0/1.5 |
|   |   |   |   | 20 | >61.1/9.7 | >529.9 | 0/1.5 |
|   |   |   |   | 10 | 15.5/9.7 | 59.8 | 0/1.5 |
|   |   |   |   | 8 | 16.0/9.7 | 64.9 | 2.5/1.5 |
|   |   |   |   | 6 | 14.0/9.7 | 44.3 | 2.0/1.5 |
|   |   |   |   | 4 | 13.0/9.7 | 34.0 | 2.8/1.5 |
|   |   |   |   | 2 | 12.5/9.7 | 28.9 | 4.0/1.5 |
|   |   |   |   | 1 | 12.0/9.7 | 23.7 | 4.5/1.5 |
| 6 | C | C | B | 300 | 13.0/8.5 | 52.9 | 0.3/4.0 |
|   |   |   |   | 200 | 15.1/8.5 | 77.6 | 2.0/4.0 |
| 7 | B | B | A | 10 | 18.7/9.3 | 101.1 | 0/3.7 |
|   |   |   |   | 8 | >47.0/9.3 | >405.4 | 0/3.7 |
|   |   |   |   | 4 | >47.0/9.3 | >405.4 | 0/3.7 |
|   |   |   |   | 2 | 14.7/9.3 | 58.1 | 0.8/3.7 |
|   |   |   |   | 1 | 18.5/9.3 | 98.9 | 4.6/3.7 |
| 8 | E | A | A | 10 | >47.0/9.7 | >384.5 | 0/4.2 |
|   |   |   |   | 5 | 14.3/9.7 | 47.4 | 1.0/4.2 |
|   |   |   |   | 2.5 | 12.5/9.7 | 28.9 | 3.3/4.2 |
| 9 | F | B | A | 16 | >53.7/10.7 | >401.8 | 0/2.5 |
|   |   |   |   | 8 | 18.0/10.7 | 68.2 | 0/2.5 |
| 10 | C | C | C | 2 | 13.6/8.5 | 60.0 | |
|   |   |   |   | 1 | 12.6/8.5 | 48.3 | |
|   |   |   |   | 0.5 | 12.8/8.5 | 50.6 | |
|   |   |   |   | 0.25 | 10.2/8.5 | 20.0 | |
| 11 | D | A | A | 200 | 16.6/8.0 | 107.5 | 1.4/3.1 |
|   |   |   |   | 150 | 14.1/8.0 | 83.4 | 1.9/3.1 |
|   |   |   |   | 100 | 13.9/8.0 | 80.7 | 4.6/3.1 |
|   |   |   |   | 50 | 12.0/8.0 | 55.6 | 2.8/3.1 |
| 12 | F | B | D | 400 | 13.4/10.7 | 25.0 | 3.4/2.5 |
|   |   |   |   | 200 | 15.0/10.7 | 40.0 | 4.0/2.5 |
|   |   |   |   | 100 | 13.9/10.7 | 30.0 | 3.0/2.5 |

It will be clearly appreciated from the test results of Table 1 that the new nitrosourea derivatives according to this invention gave a significant increase in life-span in therapeutic treatment of the leukemia in comparison with daunomycin which has been used clinically for the treatment of the leukemia and showed no or only a little accumulation of ascites. The new nitrosourea derivatives according to this invention are further characterized by their low toxicity, thus satisfying their practical application for treating leukemia and tumor diseases. For example, a typical nitrosourea derivative, 1-(2-chloroethyl)-3-(β-D-glucopyranosyl)-1-nitrosourea, showed $LD_{50}$ value of about 25 mg/kg in the intraperitoneal administration to $BDF_1$ mice.

The new nitrosourea derivatives according to this invention are prepared simply by nitrosating the corresponding urea derivatives in a known manner per se.

According to a further aspect of this invention, therefore, there is provided a process for the preparation of nitrosourea derivatives of the formula:

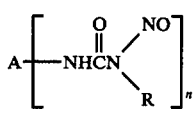 (I)

wherein A represents a glycosyl group, a monovalent residue of methyl glucoside from which the 2-hydroxy group has been removed, a monovalent residue of alditol from which the 2-hydroxy group has been removed, N-substituted carbamoyloxyalkyl group or a hydroxy-substituted cyclohexyl group when $n$ is 1 or A represents a tetravalent residue of ribostamycin from which the four amino groups have been removed when $n$ is 4 and R represents a lower alkyl group or a halo-substituted lower alkyl group, provided that R is not methyl group when A is glucosyl group which comprises treating a compound of the formula:

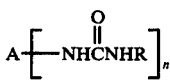 (II)

wherein A, R and $n$ have the meanings defined above with a nitrosating agent.

In the process of this invention, the nitrosation reaction may be carried out in a known manner per se by using as nitrosating agent an alkali metal nitrite, nitrogen trioxide, dinitrogen tetroxide and the like. Preferably, the alkali metal nitrite is sodium or potassium nitrite. The reaction may usually be conducted at a temperature of about $-10°$ C to $30°$ C and preferably under an acidic conditions, for example, at a pH value of about 1 to 3. Under these conditions, the reaction time is suitably about 1 to 12 hours. As reaction medium, water, a lower alkanoic acid such as formic, acetic or propionic acid or a mixture thereof may suitably be used.

After the completion of the nitrosation reaction, the reaction product may, if desired, be purified by a conventional way, for example, by using a cation exchange resin, then lyophilized followed by recrystallization from a suitable solvent to yield the desired product with a high purity.

The compounds of the formula II to be used as starting material in the process according to this invention are also new compounds in themselves and may be prepared generally by reacting a compound of the formula:

 (III)

wherein A has the meaning defined above with a lower alkyl or a halo-substituted lower alkyl isocyanate of the formula:

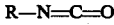 (IV)

wherein R has the meaning defined above. Before the reaction, the alcoholic hydroxy groups contained in the group A may, if necessary, be protected by a variety of OH-protecting groups known per se, typically acetyl.

As the compounds of the formula IV, there may be used a wide variety of isocyanates. Typical examples of the isocyanates of the formula IV include methyl, ethyl, n-propyl, i-propyl, n-butyl, i-butyl, sec-butyl, tert-butyl, chloromethyl, β-chloroethyl, γ-chloropropyl, β-chloropropyl, δ-chlorobutyl and β-bromoethyl isocyanates.

Thus, the starting compounds of the formula II to be used for the preparation of the compounds of the formula Ia, Ib, Ic where $A^3$ represents a glycosyl group, Id where $A^4$ represents mannopyranosyl group and If may be prepared in common by reacting O-acetyl-glycopyranosyl amine with an isocynate of the formula IV in an inert organic solvent such as methanol followed by deacetylating the reaction product. As a typical example of this preparation, one route for the preparation of 1-(β-D-mannopyranosyl)-3-methylurea is explained below. Penta-O-acetyl-D-mannopyranose of the formula:

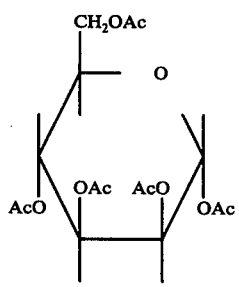

wherein Ac represents acetyl group which may be prepared by a known method [P. A. Levene, et al.: J. Biol. Chem., 90, 89 (1931)] is used as starting material and is treated, in order, with HBr and $NaN_3$ in $CH_3CN$ and then hydrogenated in the presence of Raney nickel catalyst to produce the compound of the formula:

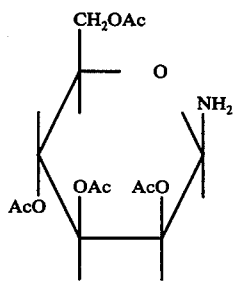

wherein Ac has the meaning defined above, which is then treated with the compound $CH_3NC=O$ to produce the compound of the formula:

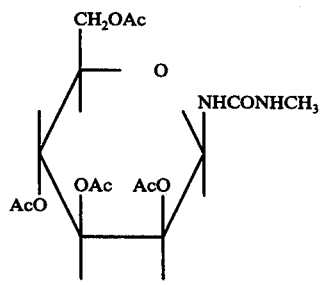

wherein Ac has the meaning defined above, which is then deacetylated to give the desired compound of the formula:

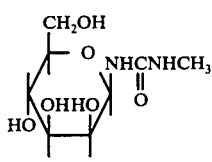

The starting compounds of the formula II to be used for the preparation of the compounds of the formula Id wherein $A^4$ represents methyl 2,6-dideoxy-$\beta$-D-glucopyranoside residue of the formula:

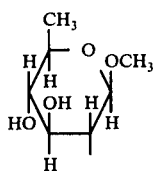

may be prepared, for example, by the following method.

The compound of the formula:

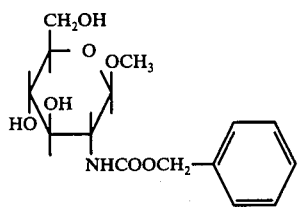

which may be prepared by a known method [A. Neuberger, et al.: J. Chem. Soc., 122 (1937)] is used as starting material and is treated with tosyl chloride or mesyl chloride to form the compound of the formula:

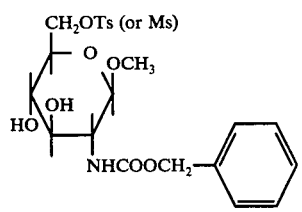

wherein Ts represents tosyl group and Ms represents mesyl group, which is treated with sodium iodide to form the compound of the formula:

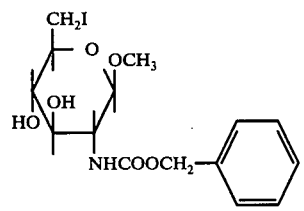

which is then hydrogenated in the presence of Raney nickel catalyst and then reacted with an isocyanate of the formula IV to give the desired compound of the formula:

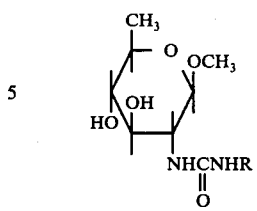

wherein R has the meaning defined above.

The compounds of the formula II to be used for the preparation of the compounds of the formula Id where $A^4$ is methyl 2-deoxy-6-O-mesyl-$\beta$-D-glucoside residue of the formula:

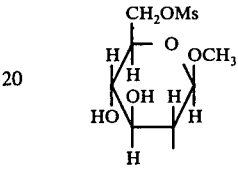

wherein Ms represents mesyl group may be prepared, for example, by the following method.

The compound of the formula:

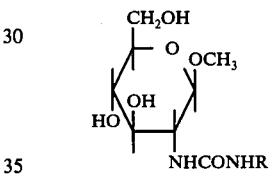

wherein R has the meaning defined above which may be prepared by a known method [T. Suami, et al: Bull. Chem. Soc. Japan, 43, 3013 (1970)] is used as starting material and is mesylated with mesyl chloride to form the desired compound of the formula:

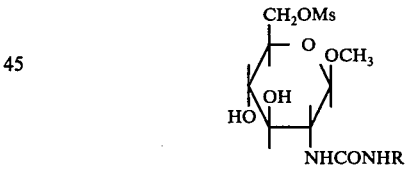

wherein Ms represents mesyl group and R has the meaning defined above.

The starting compounds of the formula II to be used for the preparation of the compounds of the formula Ic where $A^3$ represents a hydroxy-substituted cyclohexyl group may be prepared simply by reacting a hydroxy-substituted cyclohexyl amine with an isocyanate of the formula IV. The starting hydroxy-substituted cyclohexyl amine may be prepared by a known method [T. Suami and S. Ogawa: Bull. Chem. Soc. Japan, 37, 194 (1964)].

The starting compounds of the formula II to be used for the preparation of the compounds of the formula Ie may be prepared in the same way as that last-mentioned, namely by reacting an inosamine with an isocyanate of the formula IV in an inert organic solvent such as methanol. As inosamine, there may be used various isomers including scyllo-, allo-, myo-, muco-, cis-, neo-, chiro-, and epi-inosamines. Alternatively, deoxy-inosamines such as mono-, di-, tri-, and tetra-deoxy-inosamines may be used for the reaction with an isocyanate of the formula IV.

The starting compounds of the formula II to be used for the preparation of the compounds of the formula Ig may be prepared by reacting an aminoalditol of the formula:

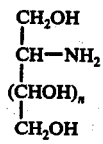

with an isocyanate of the formula IV in an inert solvent such as water, methanol, ethanol and acetone. As typical examples of aminoalditols there may be mentioned aminotritols, aminotetritols, aminopentitols and aminohexitols. Most typical aminohexitols are glucosaminol and galactosaminol.

The starting compounds of the formula II to be used for the preparation of the compounds of the formula Ih may be prepared, for example, by reacting an alkanolamine of the formula:

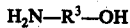

wherein $R^3$ represents an alkylene group having 2-5 carbon atoms with an isocyanate of the formula IV in an inert organic solvent such as methanol, ethanol and acetone.

The starting compounds of the formula II to be used for the preparation of the compounds of the formula Ii may be prepared, for example, by a method known per se which comprises the following steps:

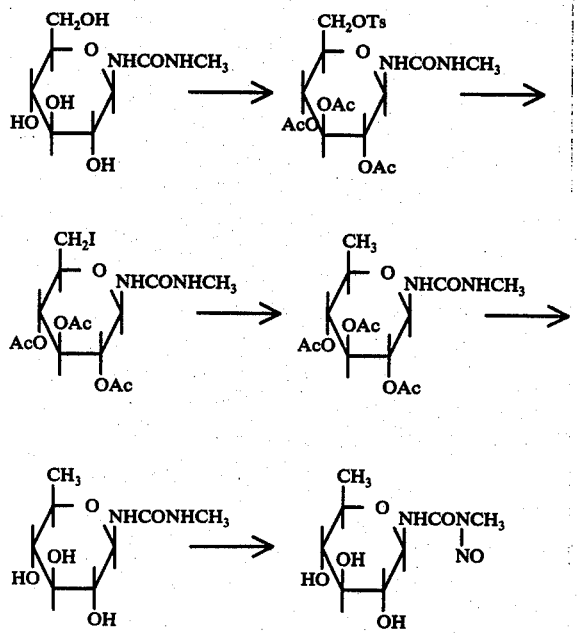

The starting compounds of the formula II to be used for the preparation of the compounds of the formula Ij may be prepared simply by reacting ribostamycin with an isocyanate of the formula IV in an inert organic solvent such as methanol.

The new nitrosourea derivatives according to this invention are also useful as intermediates for the preparation of certain other chemicals useful for pharmaceutical purposes.

The new nitrosourea derivatives of the formula I according to this invention may be easily converted to corresponding acetyl derivatives by treating them with a mixture of pyridine and acetic anhydride.

The present invention is now illustrated with reference to the following Examples to which the present inventon is not limited in any way.

EXAMPLE 1

(a) 1-ethyl-3-(β-D-glucopyranosyl)-1-nitrosourea 1-ethyl-3-(β-D-glucopyranosyl)urea (930 mg) was dissolved in a mixture of water (4.3 ml) and acetic acid (4.3 ml), and to the solution was added 370 mg (1.5 mol. equivalents) of sodium nitrite in small portions under stirring. The mixture was stirred overnight at ambient temperature to complete the nitrosation. The reaction mixture was then treated with 4 ml of a cation-exchange resin, Amberlite IR-120 (H+ form), to remove the sodium ion therefrom. The reaction mixture was subsequently freeze-dried, affording 1.0 g of the titled compound as an amorphous substance of pale yellow color. $[\alpha]_D^{26}$ −2° (c 1.0, H₂O). This substance gave a single spot at Rf 0.82 in a thin layer chromatography on silica gel using chloroform-methanol (3:2 by volume) as eluent.

N.M.R. spectrum (in D₂O): τ 4.74 (d, 1H, J 9 Hz, H-1), 8.99 (t 3H, J 7 Hz, C—CH₃).

(b) 1-ethyl-3-(tetra-O-acetyl-β-D-glucopyranosyl)-1-nitrosourea 1-ethyl-3-(β-D-glucopyranosyl) -1-nitrosourea (1.0 g) was dissolved in a mixture of pyridine (6 ml) and acetic anhydride (6 ml), and the resulting solution was allowed to stand at ambient temperature overnight to complete the acetylation. The reaction mixture was concentrated to dryness under a reduced pressure, and the residue was crystallized from ethanol. The titled compound was obtained in a yield of 1.0 g (67%). mp. 116°-118° C. $[\alpha]_D^{24}$ −8° (c 1.0, chloroform)

Elemental analysis: Calcd. for $C_{17}H_{25}N_3O_{11}$: C, 45.63; H, 5.64; N, 9.39%. Found: C, 45.89; H, 5.60; N, 9.34%.

EXAMPLE 2

(a) 1-(β-D-glucopyranosyl)-3-nitroso-3-n-propylurea 1-(β-D-glucopyranosyl)-3-n-propylurea (1.50 g) was dissolved in a mixture of water (10 ml) and acetic acid (2 ml), and to the resulting solution was added 560 mg (1.5 mol. equivalents) of sodium nitrite at ambient temperature under stirring to effect the nitrosation. The reaction mixture was treated with Amberlite IR-120 (H+ form) for the removal of sodium ion and then concentrated to dryness below 35° C and under a reduced pressure. Crystallisation of the residue from n-propanol gave 1.35 g of the titled compound. Yield 80%. mp. 112° C (decomposition with foaming). $[\alpha]_D^{21}$ −6° (c 1.0, H₂O).

Elemental analysis: Calcd. for $C_{10}H_{19}N_3O_7$: C, 40.95; H, 6.54; N, 14.33%. Found: C, 40.77; H, 6.69; N, 13.93%.

IR. spectrum: 3300 (attributable to OH), 1700 (attributable to CO), 1530 (attributable to NH) and 1490 cm$^{-1}$ (attributable to N-NO)

N.M.R. spectrum: (in $D_2O$): $\tau$ 4.77 (d, 1H, J 9 Hz, H-1), 9.22 (t, 3H, J 7 Hz, C—CH$_3$)

(b) 1-(tetra-O-acetyl-β-D-glucopyranosyl)-3-nitroso-3-n-propylurea 1-(β-D-glucopyranosyl)-3-nitroso-3-n-propylurea was acetylated in the same manner as in Example 1(b), giving the titled compound. mp. 111° C. $[\alpha]_D^{24}$ −10° (c 0.5, chloroform).

EXAMPLE 3

(a) 1-n-butyl-3-(β-D-glucopyranosyl)-1-nitrosourea 1-n-butyl-3-(β-D-glucopyranosyl)urea (0.50 g) was dissolved in a mixture of water (2 ml) and acetic acid (2 ml), and to the resulting solution was added sodium nitrite (186 mg, 1.5 mol. equivalents). The nitrosation was conducted in the same manner as in Example 1(a). The reaction mixture was treated with Amberlite IR-120 (H$^+$ form) for the removal of sodium cation and then freeze-dried, affording 0.5 g of the titled compound as a glassy substance of pale yellow color. $[\alpha]_D^{26}$ −1.5° (c 1.0, $H_2O$). This substance gave a single spot at Rf 0.51 in a thin layer chromatography on silica gel using chloroform-methanol (4:1 by volume) as eluent.

N.M.R. spectrum (in $D_2O$): $\tau$ 4.74 (d, 1H, J 7.5 Hz, H-1), 9.13 (t, 3H, J 6.5 Hz, C—CH$_3$).

(b) 1-n-butyl-3-(tetra-O-acetyl-β-D-glucopyranosyl)-1-nitrosourea 1-n-butyl-3-(β-D-glucopyranosyl)-1-nitrosourea was acetylated in the same manner as in Example 1(b). The titled compound was obtained. mp. 127°-128° C. $[\alpha]_D^{24}$ −12° (c 1.0, chloroform).

EXAMPLE 4

(a) 1-(2-chloroethyl)-3-(β-D-glucopyranosyl)-1-nitrosourea

A solution of 0.60 g of 1-(2-chloroethyl)-3-(β-D-glucopyranosyl)urea in 15 ml of 99% formic acid was admixed with 282 mg of sodium nitrite under ice-cooling and stirring. The mixture was stirred for 1 hour under ice-cooling to effect the nitrosation. The reaction mixture, after addition of 15 ml of cold water thereto, was ice-cooled for 30 minutes and then treated with 5 ml of Amberlite IR-120 (H$^+$ form) for the removal of sodium cation. The reaction mixture so treated was concentrated to dryness below 30° C by distilling off the solvent under a reduced pressure. The residue was taken up into a small volume of n-propanol and the solution was admixed with a volume of petroleum ether to give precipitate. The precipitate which deposited was collected by filtration and then dried in a desiccator under vacuum, affording 0.65 g of the titled compound as an amorphous solid of pale yellow color. Yield 92%. mp. 85° C (decomposition). $[\alpha]_D^6$ −14° (c 0.5, methanol).

Elemental analysis: Calcd. for $C_9H_{16}N_3ClO_7$: C, 34.46; H, 5.14; N, 13.40; Cl, 11.30%. Found: C, 34.36; H, 5.09; N, 13.20; Cl, 11.33%.

(b) 1-(2-chloroethyl)-3-(tetra-O-acetyl-β-D-glucopyranosyl)-1-nitrosourea 1-(2-chloroethyl)-3-(β-D-glucopyranosyl)-1-nitrosourea was treated with acetic anhydride in the same manner as in Example 1(a), giving the titled compound. mp. 103°-105° C $[\alpha]_D^{17}$ −20° (c 0.5, methanol).

EXAMPLE 5

1-(2-chloroethyl)-3-(β-D-mannopyranosyl)-1-nitrosourea 1-(2-chloroethyl)-3-(β-D-mannopyranosyl)urea (500 mg) was dissolved in 10 ml of 99% formic acid, and the resulting solution was admixed with 250 mg of sodium nitrite in an ice-bath under stirring, while the sodium nitrite was added in small portions to said solution. The mixture was agitated for 1 hour and then admixed with 10 ml of cold water, followed by agitation for further 30 minutes to complete the nitrosation. The reaction solution was treated with 20 ml of Amberlite IR-120 (H$^+$ form) and was then agitated for 20 minutes for the removal of sodium cation. After the cation-exchange resin was filtered off from the reaction mixture, the filtrate was concentrated to dryness by evaporating the solvent under a reduced pressure. A crystalline solid was yielded. This solid was digested with ethanol to give the titled compound. Yield 308 mg (55.9%). mp. 98°-100° C (decomposition with foaming). $[\alpha]_D^{25}$ −10° (c 0.5, $H_2O$).

Elemental analysis: Calcd. for $C_9H_{16}N_3ClO_7$ (M.W. 313.69): C, 34.46; H, 5.14; N, 13.40; Cl, 11.30%. Found: C, 35.21; H, 5.61; N, 11.69; Cl, 12.07%.

EXAMPLE 6

(a) 1-(2-chloroethyl)-3-(β-D-galactopyranosyl)-1-nitrosourea

To a solution of 300 mg of 1-(2-chloroethyl)-3-(β-D-galactopyranosyl)urea in 2 ml of 99% formic acid was slowly added 150 mg of sodium nitrite in an ice-bath under stirring. The mixture was stirred for 1 hour under ice-cooling to complete the nitrosation. The reaction mixture was admixed with 50 ml of ethyl ether to deposit an oily substance. The ethyl ether phase was separated from the oily substance by decantation. The operation of adding ethyl ether to and separating the ethyl ether phase from the oily substance by decantation was repeated three times, using 50 ml, 20 ml and 20 ml of the ether, respectively. Thereafter, the oily substance was taken up into 30 ml of methyl alcohol, and the resultant solution was admixed with 3 ml of Amberlite IR-120 (H$^+$ form). The admixture was filtered to remove cation-exchange resin, and the filtrate was concentrated under a reduced pressure, depositing crystals of the titled compound. Yield 210 mg (63.6%). mp. 145° C (decomposition with foaming). $[\alpha]_D^{21.0}$ +13.0° (c 0.5, $H_2O$).

IR. spectrum: 1720, 1535 (ureido) and 1495 cm$^{-1}$ (nitrosamine)

N.M.R. spectrum: δ 3.52 (t, 2H, J 7 Hz, N—CH$_2$—CH$_2$—Cl) δ 4.28 (t, 2H, J 7 Hz, N—CH$_2$—CH$_2$—Cl) δ 6.03 (t, 1H, $J_{NH} = J_{1,2}$ 9 Hz, H-1) δ 10.57 (d, 1H, J 9 Hz, NH)

Elemental analysis: Calcd. for $C_9H_{16}N_3ClO_7$ (M.W. 313.5): C, 34.46; H, 5.14; N, 13.40; Cl, 11.30%. Found: C, 34.58; H, 5.09; N, 13.12; Cl, 11.22%.

(b)
1-(2-chloroethyl)-3-(tetra-O-acetyl-β-D-galac-
topyranosyl)-1-nitrosourea 1-(2-chloroethyl)-3-(β-D-galactopyranosyl)-1-nitrosourea (115 mg) was dissolved in 2 ml of anhydrous pyridine, and to the resulting solution was added dropwise 1 ml of acetic anhydride under ice-cooling and stirring. The mixture was stirred for 5 hours under ice-cooling to complete the acetylation. The acetylation reaction mixture was concentrated to dryness under a reduced pressure, and the residue was crystallized from water, affording the titled compound. Yield 138 mg (78.1%). mp. 69°–70° C. $[\alpha]_D^{19.5}$ +5.0° (c 0.5, chloroform).

EXAMPLE 7

(a) 1-methyl-3-(β-D-xylopyranosyl)urea 2,3,4-tri-O-acetyl-β-D-xylopyranosyl azide (1.03 g; 3.4 mmol) was dissolved in ethyl acetate (10 ml) and subjected to catalytic hydrogenation in the presence of platinum oxide (29 mg) as catalyst at ambient temperature for 1 hour, the initial hydrogen pressure being at 50 psi, thus converting the azido group to amino group.

Thin layer chromatography of the reaction product on silica gel using toluene-methyl ethyl ketone (1:1 by volume) as eluent gave no spot at Rf 0.84 which is of the starting material, but a single spot at Rf 0.39.

After the removal of the catalyst by filtration, the reaction mixture was washed with ethyl acetate (10 ml) and the filtrate was combined with the washings, to which was then added methyl isocyanate (0.8 ml; 12.8 mmol) and the resulting mixture was stirred for 1.5 hours under ice-cooling and then allowed to stand overnight at ambient temperature.

Thin layer chromatography of the reaction product on silica gel using benzene-ethanol (5:1 by volume) as eluent gave no spot at Rf 0.62 which is of the starting material, but a main spot at Rf 0.53.

After the removal of the solvent by distillation under a reduced pressure, the reaction product was crystallized from isopropanol to give crude crystals (979 mg). mp. 165°–168° C. Recrystallization from isopropanol gave 1-methyl-3-(2,3,4-tri-O-acetyl-β-D-xylopyranosyl)urea (801 mg) in pure state. Yield 70.7%. mp. 170°–172° C. $[\alpha]_D^{20}$ +43° (c 1.4, chloroform).

The compound (560 mg) thus obtained was dissolved in methanol (1.5 ml), to which was added 0.1N sodium methoxide (2 ml) and the resulting mixture was stored overnight in a refrigerator to effect the deacetylation. The precipitate so deposited was collected by filtration to yield crude crystals (284 mg). Recrystallization from methanol gave the titled compound (205 mg). Yield 61.9%. mp. 197.5°–198.0° C (with decomposition). $[\alpha]_D^{20}$ −27.3° (c 0.7, $H_2O$).

Elemental analysis: Calcd. for $C_7H_{14}N_2O_5$: C, 40.77; H, 6.84; N, 13.59%. Found: C, 40.50; H, 6.67; N, 13.26%.

(b) 1-methyl-1-nitroso-3-(β-D-xylopyranosyl)urea 1-methyl-3-(β-D-xylopyranosyl)urea (418 mg, 2.0 mmol) and sodium nitrite (174 mg, 2.5 mmol) were dissolved in water (3 ml) and to the resulting mixture was added glacial acetic acid (0.5 ml) under stirring and ice-cooling and maintained under the same conditions for further 2 hours and then stored overnight in a refrigerator.

Thin layer chromatography of the reaction product on silica gel using chloroform-methanol (3:1 by volume) gave no spot at Rf 0.19 which is of the starting material, but a single spot at Rf 0.60.

After a treatment with Amberlite IR-120 ($H^+$ form) in a known manner for the removal of the sodium cation followed by a distillation under a reduced pressure for the removal of the solvent used, there was obtained a crystalline residue. Digestion of the residue with ethanol gave the titled compound (299 mg). Yield 62.7%. mp. 109°–110° C (with decomposition). $[\alpha]_D^{18}$ − 26.8° (c 0.6, $H_2O$).

IR. spectrum ($cm^{-1}$): 1485 (N—NO)

Elemental analysis: Calcd. for $C_7H_{13}N_3O_6$: C, 35.74; H, 5.57; N, 17.87%. Found: C, 35.92; H, 5.54; N, 17.65%.

(c)
1-methyl-1-nitroso-3-(2,3,4-tri-O-acetyl-β-D-xylopyranosyl)urea 1-methyl-1-nitroso-3-(β-D-xylopyranosyl)urea (110 mg) was dissolved in a mixture of pyridine (1 ml) and acetic anhydride (1 ml) and the resulting mixture was allowed to stand at room temperature for effecting the acetylation. The reaction mixture was then concentrated under a reduced pressure to give a crystalline residue which was then crystallized from ethanol, yielding the titled compound (147 mg). Yield 87.0%. mp. 127°–127.5° C (with decomposition). $[\alpha]_D^{20}$ −25.4° (c 0.7, chloroform).

I.R. spectrum ($cm^{-1}$): 1495 (N—NO)

EXAMPLE 8

(a) 1-(2-chloroethyl)-3-(β-D-xylopyranosyl)urea 2,3,4-tri-O-acetyl-β-D-xylopyranosyl azide (1.94 g, 6.4 mmol) was dissolved in ethyl acetate (15 ml) and subjected to catalytic hydrogenation in the presence of platinum oxide (45 mg) as catalyst at ambient temperature for 1 hour at an initial hydrogen pressure of 50 psi, thus converting the azide group to amino group.

Thin layer chromatography of the reaction product on silica gel using toluene-methyl ethyl ketone (1:1 by volume) as eluent gave no spot at Rf 0.84 which is of the starting compound, but a single spot at Rf 0.39.

After the removal of the catalyst by filtration, the reaction mixture was washed with ethyl acetate (10 ml) and the filtrate was combined with the washings, to which was then added 2-chloroethyl isocyanate (1.5 ml, 17.7 mmol) and the resulting mixture was stirred for 1.5 hours under ice-cooling.

Thin layer chromatography of the reaction product on silica gel using toluene-methyl ethyl ketone (1:1 by volume) as eluent gave a main spot at Rf 0.52 and a small spot at Rf 0.40.

The reaction mixture was concentrated under a reduced pressure to remove the solvent used leaving a syrup, to which was added 0.1N sodium methoxide (7 ml) and the homogeneous mixture thus formed was allowed to stand in a refrigerator to effect the deacetylation. The precipitate so deposited was collected by filtration to yield crude crystals (1.25 g). Recrystallization from methanol gave the titled compound (768 mg). Yield 46.9%. mp. 153°–155° C (with decomposition). $[\alpha]_D^{21}$ −11.0° (c 1.1, $H_2O$).

Further recrystallization gave a sample of analytical purity. mp. 159.5°–160° C (with decomposition). $[\alpha]_D^{20}$ −13.0° (c 0.7, $H_2O$).

(b)
1-(2-chloroethyl)-1-nitroso-3-(β-D-xylopyranosyl)urea 1-(2-chloroethyl)-3-(β-D-xylopyranosyl)urea (314 mg, 1.2 mmol) was dissolved in 99% formic acid (3 ml), to which was then added sodium nitrite (173 mg, 2.5 mmol) and the resulting mixture was stirred for 2 hours under ice-cooling.

Thin layer chromatography of the reaction product on silica gel using chloroform-ethanol (2:1 by volume) as eluent gave no spot at Rf 0.31 which is of the starting compound, but a main spot at Rf 0.63.

To the reaction mixture was added water (1 ml) and the mixture, after standing for 5 minutes, was treated with Amberlite IR-120 (H$^+$ form) to remove the sodium ion therefrom. After a distillation under a reduced pressure for the removal of the solvent used followed by digesting with ethylether, there was obtained a hygroscopic amorphous solid mass (264 mg). Yield 75.5%. mp. 84°–85° C (with decomposition). $[\alpha]_D^{22}$ −8.0° (c 0.5, H$_2$O).

Elemental analysis: Calcd. for C$_8$H$_{14}$N$_3$O$_6$Cl: C, 33.87; H, 4.97; N, 14.81; Cl, 12.50%. Found: C, 34.17; H, 5.10; N, 14.44; Cl, 12.80%.

(c)
1-(2-chloroethyl)-1-nitroso-3-(2,3,4-tri-O-acetyl-β-D-xylopyranosyl)urea 1-(2-chloroethyl)-1-nitroso-3-(β-D-xylopyranosyl)urea (99 mg) was acetylated with acetic anhydride and pyridine in the same manner as that used in Example 1(b). Crystallization from a mixture of chloroform and n-propanol yielded the titled compound (42 mg). Yield 29.4%. mp. 124.5°–125° C (with decomposition). $[\alpha]_D^{17}$ −19.0° (c 0.9, chloroform).

EXAMPLE 9

(a) 1-(1,3/2N-dihydroxycyclohexyl)-3-methylurea

2α-amino-1β,3β-cyclohexanediol (378 mg) was dissolved in water (10 ml), to which was then added methyl isocyanate (0.35 ml, 2 mol equivalents) under stirring and ice-cooling. After the completion of addition, the stirring was continued for further 1.5 hours. The reaction mixture was then concentrated under a reduced pressure and the residue was recrystallized from ethanol to give the title compound as needles (368 mg). mp. 170°–173° C. Concentration of the mother liquor under a reduced pressure gave another crop of the titled compound (96 mg). mp. 169°–172° C. Total yield 464 mg (86%).

(b)
1-(1,3/2N-dihyroxycyclohexyl)-3-methyl-3-nitrosourea 1-(1,3/2N-dihydroxycyclohexyl)-3-methylurea (308 mg, 1.6 mmol) and sodium nitrite (190 mg, 2.8 mmol) were dissolved in water (5 ml), to which was then added glacial acetic acid (1 ml) under stirring and ice-cooling. After stirring for further 1 hour under ice-cooling, the reaction mixture was allowed to stand overnight in a refrigerator.

Pale yellow crystals which were deposited from the reaction mixture were collected by filtration to yield the titled compound (65 mg). mp. 65°–67° C (with decomposition). The filtrate was treated with Amberlite IR-120 (H$^+$ form) for the removal of the sodium cation and then distilled under a reduced pressure for the removal of the solvent used, leaving a crystalline residue. The residue was digested with ethanol to yield another crop of the titled compound (203 mg) as pale yellow crystals. mp. 64°–65° C (with decomposition). Total yield 268 mg (75.4%).

IR. spectrum (cm$^{-1}$): 1715 (amide I), 1545 (amide II), 1475 (N—NO)

Elemental analysis: Calcd. for C$_8$H$_{15}$N$_3$O$_4$: C, 44.23; H, 6.96; N, 19.34%. Found: C, 44.61; H, 6.96; N, 18.77%.

(c)
1-(1,3-di-O-acetyl-1,3/2N-dihydroxycyclohexyl)-3-methyl-3-nitrosourea 1-(1,3/2N-dihydroxycyclohexyl)-3-methyl-3-nitrosourea (105 mg) was dissolved in a mixture of acetic anhydride (1 ml) and pyridine (1 ml) and the resulting mixture was allowed to stand overnight at ambient temperature. After reading the reaction mixture as in Example 1(b), the crystalline residue obtained was digested with ethylether to yield the titled compound (123 mg). Yield 84.5%. mp. 119°–120° C (with decomposition).

EXAMPLE 10

(a)
1-(2-chloroethyl)-3-(1,3/2N-dihydroxycyclohaexyl)urea

2α-amino-1β,3β-cyclohexanediol (557 mg) was suspended in 2-methoxyethanol (30 ml) containing methyl cellosolve and to the resulting mixture was added 2-chloroethyl isocyanate (1 ml, 2.7 mol equivalents) in small portions under stirring and ice-cooling. The stirring was continued for further 1.5 hours to give a transparent solution which was then concentrated under a reduced pressure, yielding a crystalline residue. Recrystallization from a mixture of methanol and n-propanol gave the titled compound (670 mg). Yield 67%. mp. 125°–126.5° C (with decomposition).

(b)
1-(2-chloroethyl)-3-(1,3/2N-dihydroxycyclohexyl)-1-nitrosourea 1-(2-chloroethyl)-3-(1,3/2N-dihydroxycyclohexyl)urea (426 mg, 1.8 mmol) was dissolved in 99% formic acid (6 ml), to which was then added sodium nitrite (204 mg, 3.0 mmol) under stirring and ice-cooling and the resulting mixture was stirred for further 2 hours under ice-cooling.

The reaction mixture was a transparent yellow solution and thin layer chromatography thereof on silica gel using chloroform-ethanol (6:1 by volume) as eluent gave no spot at Rf 0.51 which is of the starting compound, but a main spot at Rf 0.71.

To the reaction mixture was added water (2 ml) and the resulting mixture, after standing for 5 minutes, was treated with Amberlite IR-120 (H$^+$ form) for the removal of the sodium cation and then distilled under a reduced pressure for the removal of the solvent used, leaving a residue. Recrystallization from a mixture of ethanol and ethylether gave the titled compound (281 mg) as pale yellow crystals. Yield 58.7%. mp. 125°–125.5° C (with decomposition).

IR. spectrum (cm$^{-1}$): 1700 (amide I), 1555 (amide II), 1500 (N—NO)

Elemental analysis: Calcd. for C$_9$H$_{16}$N$_3$O$_4$Cl: C, 40.68; H, 6.07; N, 15.82; Cl, 13.34%. Found: C, 40.51; H, 5,87; N, 15.70; Cl, 13.13%.

(c)
1-(2-chloroethyl)-3-(1,3-di-O-acetyl-1,3/2N-dihydroxycyclohexyl)-1-nitrosourea 1-(2-chloroethyl)-3-(1,3/2N-dihydroxycyclohexyl)-1-nitrosourea (116 mg) was dissolved in a mixture of acetic anhydride (1 ml) and pyridine (1 ml) and the resulting mixture was allowed to stand overnight at ambient temperature. The reaction mixture was then distilled under a reduced pressure to remove the solvent used, leaving a crystalline residue which was digested with ethanol to yield the titled compound (132 mg). Yield 86.4%. mp. 151°–152° C (with decomposition).

EXAMPLE 11

1-(β-D-mannopyranosyl)-3-methyl-3-nitrosourea 1-(β-D-mannopyranosyl)-3-methyl-urea (200 mg) was dissolved in a mixture of 1.5 ml of glacial acetic acid and 3.5 ml of water, and the resulting solution was admixed with 99 mg of sodium nitrite. The mixture so obtained was agitated for 3 hours at ambient temperature to effect the nitrosation. The reaction mixture was treated with Amberlite IR-120 (H+ form) to remove sodium cation therefrom. The reaction mixture so treated was then concentrated by distillation under reduced pressure at a temperature of less than 30° C to remove the solvent, so that a crystalline product was deposited. This crystalline product was collected by filtration and washed with n-propanol, affording 180 mg of the titled compound. Yield 78%. mp. 103° C (with decomposition). $[\alpha]_D^{26}$ −12.6° (c 0.99, H$_2$O).

Elemental analysis Calcd. for C$_8$H$_{15}$N$_3$O$_7$: C, 36.23; H, 5.70; N, 15.84%. Found: C, 35.92; H, 5.70; N, 15.67%.

EXAMPLE 12

Methyl 2,6-dideoxy-2-(N'-methyl-N'-nitroso-ureido)-β-D-glycopyranoside

Methyl 2,6-dideoxy-2-(N'-methyl-ureido)-β-D-glucopyranoside (124 mg) of the formula:

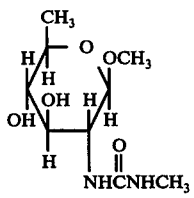

was dissolved in a mixture of 0.5 ml of glacial acetic acid and 2.5 ml of water, and the resulting solution was admixed with 55 mg of sodium nitrite at ambient temperature and under agitation to effect the nitrosation. The reaction mixture so obtained was then allowed to stand overnight in a refrigerator, so that a crystalline product was deposited. This crystalline product was collected by filtration and then washed with ethanol, affording 80 mg of methyl 2,6-dideoxy-2-(N'-methyl-N'-nitroso-ureido)-β-D-glucopyranoside as the desired product. The mother liquor was then treated with Amberlite IR-120 (H+ form) to remove the sodium ion, and the mother liquor so treated was concentrated by distilling off the solvent under reduced pressure. Crystallization of the residue from ethanol gave 45 mg of the desired product as a second crop. Yield 125 mg (90%). $[\alpha]_D^{28}$ −14° (c 0.52, H$_2$O).

Elemental analysis Calcd. for C$_9$H$_{17}$N$_3$O$_6$: C, 41.06; H, 6.51; N, 15.96%. Found: C, 41.03; H, 6.42; N, 16.00%.

EXAMPLE 13

Methyl 2-deoxy-6-O-mesyl-2-(N'-methyl-N'-nitrosoureido)-β-D-glucopyranoside

Methyl 2-deoxy-6-O-mesyl-2-(N'-methylureido)-β-D-glucopyranoside (400 mg) of the formula

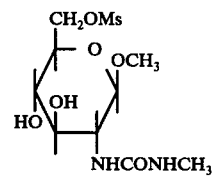

was dissolved in 50 ml of water, and the resulting aqueous solution was adjusted to pH 3 by addition of 2 ml of acetic acid. The acidified aqueous solution was admixed with 120 mg of sodium nitrite and the mixture was agitated at ambient temperature overnight to effect the nitrosation. The reaction mixture was treated with Amberlite IR-120 (H+ form) to remove the sodium ion therefrom. The reaction mixture was then evaporated under a reduced pressure at a temperature below 25° C. The residue was crystallized from ethanol to give 350 mg of the titled compound. mp. 131°–132° C (with decomposition). $[\alpha]_D^{20}$ −14° (c 0.5, dimethylsulfoxide).

Elemental analysis Calcd. for C$_{10}$H$_{19}$N$_3$SO$_9$: C, 33.61; H, 5.35; N, 11.75; S, 8.97%. Found: C, 33.87; H, 5.36; N, 11.44; S, 8.73%.

EXAMPLE 14

(a)
1-(2-chloroethyl)-3-(1N,3,5/2,4,6-pentahydroxycyclohexyl)urea

A solution of scyllo-inosamine (551 mg) in water (20 ml) was cooled in an ice-bath. To this cold solution was added 0.6 ml (2.3 mol equivalents) of 2-chloroethyl isocyanate in small portions under ice-cooling and stirring. The mixture so obtained was stirred for further 2 hours to complete the reaction. A crystalline product deposited was removed from the reaction mixture by filtration and washed with ethanol to yield 432 mg of the titled compound as crystals of a melting point of 195°–197° C (with decomposition). The filtrate from which said crystalline product was removed was then concentrated by evaporating the solvent under a reduced pressure, and the residue so obtained was digested with a volume of ethanol. 357 mg of the titled compound was obtained as a second crop. Total yield 90% (789 mg).

IR. spectrum (in KBr): 1625 (C=O) and 1580 cm$^{-1}$ (NH, amide II).

Elemental analysis: Calcd. for C$_9$H$_{17}$N$_2$O$_6$Cl: C, 37.97; H, 6.02; N, 9.84; Cl, 12.45%. Found: C, 37.96; H, 5.78; N, 9.76; Cl, 12.71%.

(b) 1-(2-chloroethyl)-1-nitroso-3-(1N,3,5/2,4,6-pentahydroxycyclohexyl)urea 1-(2-chloroethyl)-3-(1N,3,5/2,4,6-pentahydroxycyclohexyl)urea (741 mg; 2.6 mm mol) of the formula

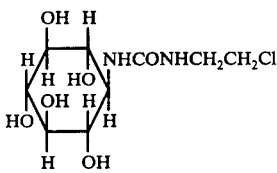

was dissolved in 25 ml of 99% formic acid, and to the resulting solution was added 262 mg (3.8 mm mol) of sodium nitrite in small portions. The mixture so obtained was stirred for 2 hours under ice-cooling to complete the nitrosation. The reaction mixture was admixed with 2 ml of water, allowed to stand for 5 minutes and then treated with Amberlite IR-120 for the removal of sodium cation. The mixture so treated was concentrated to dryness by evaporation of the solvent under a reduced pressure, leaving a crystalline residue. This residue was digested with ethanol to give 636 mg of the titled compound as pale yellow crystals. Yield 77.9%. mp. 140°–142° C (with decomposition).

IR. spectrum: 1705 (amide I), 1555 (amide II) and 1500 cm$^{-1}$ (N—NO).

Elemental analysis: Calcd. for $C_9H_{16}N_3O_7Cl$: C, 34.46; H, 5.14; N, 13.40; Cl, 11.30%. Found: C, 34.66; H, 5.15; N, 11.50; Cl, 11.50%.

(c) 1-(2-chloroethyl)-1-nitroso-3-(2,3,4,5,6-penta-O-acetyl-1N,3,5/2,4,6-pentahydroxycyclohexyl)urea 1-(2-chloroethyl)-1-nitroso-3-(1N,3,5/2,4,6-pentahydroxycyclohexyl)urea (116 mg) was acetylated in the same manner as in Example 1(b) by reacting with acetic anhydride in pyridine. The acetylating product was crystallized from ethanol, affording 171 mg of the titled compound as pale yellow crystals. Yield 88.3%. mp. 205.5°–209° C (with decomposition).

Elemental analysis: Calcd. for $C_{19}H_{26}O_{12}N_3Cl$: C, 43.56; H, 5.00; N, 8.02; Cl, 6.77%. Found: C, 43.58; H, 4.97; N, 7.79; Cl, 6.75%.

EXAMPLE 15

(a) 1-(β-D-maltosyl)-3-methylurea

To a solution of 2.5 g of 2 3,6,2′,3′,4′,6′-hepta-O-acetyl-β-D-maltosylamine (prepared from β-D-maltosylamine by A. Bertho's method of the "Ann." 562, 229 (1949) in 40 ml of dioxane was added slowly 0.7 ml of methyl isocyanate under ice-cooling and stirring. The mixture was stirred for further 3 hours and the reaction mixture was concentrated under a reduced pressure. Crystallization of the residue from isopropanol gave 2.33 g of 1-(β-D-maltosyl)-3-methylurea hepta-O-acetate. This compound (2.0 g) was dissolved in 50 ml of ammonia-saturated methanol at 0° C, and the mixture was allowed tb stand for two days at ambient temperature to complete the reaction. The reaction mixture was concentrated under a reduced pressure, and crystallization of the residue from methanol-ethanol gave the titled compound. Yield 665 mg (57.8%). m.p. 90°–92° C. $[\alpha]_D^{22.5}$ +70.0° (c 0.5, $H_2O$).

IR. spectrum: 1660 and 1570 cm$^{-1}$ (ureido).

(b) 1-(β-D-maltosyl)-3-methyl-3-nitrosourea 1-(β-D-maltosyl)-3-methylurea (300 mg) was dissolved in a mixture of 2 ml of water and 0.5 ml of glacial acetic acid, and to the resulting solution was added slowly 100 mg of sodium nitrite under ice-cooling and stirring. The solution was stirred overnight under cooling with water to complete the nitrosation. The reaction mixture was treated with a cation-exchange resin, Amberlite IR-120 for the removal of sodium ion and was then concentrated under a reduced pressure. Crystallization of the residue from emthanol-ethyl ether gave the titled compound. Yield 293 mg (91.0%). mp. 128° C (decomposition with foaming). $[\alpha]_D^{21}$ +90° (c 0.5, water).

IR. spectrum: 1730, 1550 (ureido) and 1490 cm$^{-1}$ (nitrosamine).

EXAMPLE 16

(a) 1-(2-chloroethyl)-3-(β-D-maltosyl)urea

The process of Example 15(a) was repeated using 2,3,6,2′,3′,4′,6′-hepta-O-acetyl-β-D-maltosylamine and 2-chloroethyl isocyanate. The titled compound was obtained in a yield of 46.1%. mp. 108° C (with decomposition).

(b) 1-(2-chloroethyl)-3-(β-D-maltosyl)-1-nitrosourea

To a solution of 500 mg of 1-(2-chloroethyl)-3-(β-D-maltosyl)-urea in 3 ml of aqueous 99% formic acid was added slowly 150 mg of sodium nitrite under ice-cooling and stirring. The mixture was stirred for 2 hours and the reaction mixture was then treated with Amberlite IR-120 (H$^+$ form) to remove sodium cation. After the removal of the cation-exchange resin by filtration from the reaction mixture, the filtrate was concentrated under a reduced pressure. Crystallization of the residue from emthanol-isopropanol gave the titled nitroso compound. Yield 227 mg (52.0%). mp. 96° C (decomposition with foaming). $[\alpha]_D^{23}$ +60° (c 0.5, water).

IR. spectrum: 1730, 1540 (ureido) and 1505 cm$^{-1}$ (nitrosamine)

EXAMPLE 17

(a) 1-(β-D-lactosyl)-3-methylurea

The process of Example 15(a) was repeated using 2,3,6,2′,3′,4′,6′-hepta-O-acetyl-β-D-lactosylamine and methyl isocyanate. The titled compound was obtained.

(b) 1-(β-D-lactosyl)-3-methyl-3-nitrosourea

To a solution of 500 mg of 1-(β-D-lactosyl)-3-methylurea in a mixture of 5 ml of water and 0.5 ml of glacial acetic acid was added slowly 150 mg of sodium nitrite under ice-cooling and stirring. The mixture was stirred overnight under cooling, with water, and the reaction mixture was treated with Amberlite IR-120 (H$^+$ form) for the removal of sodium cation. After filtration of the reaction mixture to remove the resin, the reaction solution (namely, the filtrate) was concentrated under a reduced pressure. Crystallization of the residue from methanol-ethanol gave the titled compound as pure crystals. Yield 440 mg (82.0%). mp. 175° C (decomposition with foaming). $[\alpha]_D^{23}$ +4.0° (c 0.5, water).

IR. spectrum: 1725, 1540 (ureido) and 1485 cm$^{-1}$ nitrosamine).

EXAMPLE 18

(a) 1-(2-chloroethyl)-3-(β-D-lactosyl)urea

The process of Example 15(a) was followed using 2,3,6,2',3',4',6'-hepta-O-acetyl-β-D-lactosylamine and 2-chloroethyl isocyanate. The titled compound was obtained. mp. 119°–120° C.

(b) 1-(2-chloroethyl)-3-(β-D-lactosyl)-1-nitrosourea

To a solution of 500 mg of 1-(2-chloroethyl)-3-(β-D-lactosyl)urea in 300 ml of aqueous 99% formic acid was added slowly 150 mg of sodium nitrite under ice-cooling and stirring. The mixture was subsequently processed in the same manner as in Example 17, affording the above titled compound. Yield 290 mg (54.5%). mp. 129° C (decomposition with foaming). $[\alpha]_D^{22.5} +4.0°$ (c 0.5, water).

IR. spectrum: 1735, 1540 (ureido) and 1500 cm$^{-1}$ (nitrosamine).

EXAMPLE 19

(a) N-carbamoyl-N'-(2-chloroethyl)-D-glucosaminol

A solution of 500 mg of D-glucosaminol in 8 ml of water was admixed with 1.5 ml (5 mol proportions) of 2-chloroethyl isocyanate under stirring and cooling with water. The admixture was stirred for one day under water-cooling. The reaction mixture was filtered under suction to remove the solid matter comprising by-products. The filtrate was admixed with 12 ml of a cation-exchange resin, Amberlite IR-120 (H$^+$ form) and was then separated from the resin by filtration. The filtrate was concentrated under a reduced pressure, and the residue was taken up into a volume of methanol. Addition of ethyl ether to the methanolic solution caused a gelly solid to deposit. This colorless solid was dissolved in a solution of sodium methoxide in methanol, which was then stored for one day under ice-cooling and was subsequently admixed with Amberlite IR-120 (H$^+$ form). When the admixture reached pH 4, it was then filtered to remove the resin. The filtrate was concentrated under a reduced pressure, leaving the residue which was then crystallized from ethanol. The titled compound as the crystals was obtained in a yield of 360.3 mg (45.1%). mp. 124°–125° C, $[\alpha]_D^{24}$ (c 1.0, methanol).

IR. spectrum: 1620 (amide I) and 1580 cm$^{-1}$ (amide II).

(b) N-carbamoyl-N'-(2-chloroethyl)-N'-nitroso-D-glucosaminol

A solution of 50 mg of N-carbamoyl-N'-(2-chloroethyl)-D-glucosaminol in 1 ml of glacial acetic acid was admixed with 27 mg (2.25 mol proportions) of sodium nitrite under ice-cooling and stirring and the mixture was stirred for 4 hours under ice-cooling to complete the nitrosation. The reaction mixture was filtered under suction to remove the solid matter comprising by-products. The filtrate was admixed with 2 ml of Amberlite IR-120 (H$^+$ form). When the admixture reached pH 1, the admixture was filtered to remove the resin. The filtrate was freeze-dried, affording the titled nitroso compound. Yield 31 mg (56.3%). mp. 73°–74° C. $[\alpha]_D^{20}$ +22.8° C (c 0.5, methanol).

IR. spectrum: 1710 (amide I), 1540 (amide II) and 1490 cm$^{-1}$ (N-nitroso group.)

Elemental analysis: Calcd. for C$_9$H$_{18}$O$_7$N$_3$Cl: C, 34.24; H, 5.74; N, 13.31; Cl, 11.23%. Found: C, 33.22; H, 5.45; N, 12.52; Cl, 10.79%.

EXAMPLE 20

(a) (N-carbamoyl-N'-methyl)-O-(O-carbamoyl-N-methyl)-ethanolamine

To a solution of 10 ml of ethanolamine in 40 ml of methanol was gradually added 24 ml (2.5 molar proportions) of methyl isocyanate in an ice bath. The mixture was agitated for 3 hours to deposit a crystalline product. The whole mixture was stored overnight in a refrigerator and was then filtered, affording the titled compound as white colored crystals. Yield 11.11 g (38.3%). mp. 133°–134° C. $[\alpha]_D^{22}$ −4° (c 1.0, H$_2$O).

IR. spectrum: 1700 (ester), 1630 (C=O amide I) and 1590 cm$^{-1}$ (amide II)

Elemental analysis: Calcd. for C$_6$H$_{13}$N$_3$O$_3$: C, 41.14; H, 7.48; N, 23.99%. Found: C, 41.25; H, 7.32; N, 24.16%.

(b) (N-carbamoyl-N'-methyl-N'-nitroso)-(O-carbamoyl-N-methyl)-ethanolamine

To a solution of 2 g of (N-carbamoyl-N'-methyl)-O-(O-carbamoyl-N-methyl)-ethanolamine in 2 ml of glacial acetic acid was added slowly a solution of 1.73 g (2.2 molar proportion) of sodium nitrite in 45 ml of water in an ice bath. The mixture was stirred for 1 hour to complete the nitrosation. The reaction mixture was filtered to remove the white colored crystals deposited. The filtrate was admixed with 50 ml of a cation-exchange resin, Amberlite IR-120 (H$^+$ form). When the admixture reached pH 2, it was then filtered to remove the resin. The filtrate was concentrated to dryness by evaporating the solvent below 30° C under a reduced pressure. The residue was crystallized from acetone to give the yellow colored needles. Recrystallization of the crystals from methanol gave the titled desired compound. Yield 1.694 g (72.7%). mp. 97° C (decomposition with foaming). $[\alpha]_D^{22}$ −0.4° (c 1.0, methanol).

IR. spectrum: 1730 (ester & amide I), 1530 (amide II) and 1480 cm$^{-1}$ (N-nitroso group).

Elemental analysis: Calcd. for C$_6$H$_{12}$N$_4$O$_4$: C, 35.29; H, 5.93; N, 27.44%. Found: C, 35.45; H, 5.85; N, 27.75%.

EXAMPLE 21

(a) (N-carbamoyl-N'-2-chloroethyl)-(O-carbamoyl-N'-2-chloroethyl)-ethanolamine The process of Example 20(a) was repeated using 2 ml of ethanolamine and 4 ml of 2-chloroethyl isocyanate. The titled compound was obtained in a yield of 1.999 g (22.4%). mp. 124°–126° C. $[\alpha]_D^{24}$ +64° (c 1.0, acetone).

IR. spectrum: 1700 (ester), 1630 (amide I) and 1590 cm$^{-1}$ (amide II).

Elemental analysis: Calcd. for C$_8$H$_{15}$O$_3$N$_3$Cl$_2$: C, 35.31, H, 5.56; N, 15.44; Cl, 26.05%. Found: C, 35.54; H, 5.52; N, 15.36; Cl, 26.07%.

(b) (N-carbamoyl-N'-2-chloroethyl-N'-nitroso)-(O-carbamoyl-N'-2-chloroethyl)-ethanolamine To a solution of 200 mg of (N-carbamoyl-N'-2-chloroethyl)-(O-carbamoyl-N'-2-chloroethyl)-ethanolamine of Example 20(b) in 4 ml of glacial acetic acid was added slowly 200 mg (3.9 mol proportions) of sodium nitrite in an ice bath. The mixture was stirred for 2 hours under ice-cooling to complete the nitrosation. The reaction mixture was filtered to remove the insoluble matter, and the filtrate was admixed with 14 ml of Amberlite IR-120 (H$^+$ form). When the admixture reached pH 1, it was then filtered to remove the resin. The filtrate was concentrated under a reduced pressure and the resulting oily residue was crystallized from a mixture of chloroform and isopropanol to give the titled compound as yellow colored crystals. Yield 149.7 mg (67.6%). mp. 64°–65° C. $[\alpha]_D^{20}$ +4° (c 0.5, methanol).

IR. spectrum: 1700 (ester & amide I), 1530 (amide II) and 1490 cm$^{-1}$ (N-nitroso group).

Elemental analysis Calcd. for $C_8H_{14}O_4N_4Cl_2$: C, 31.90; H, 4.69; N, 18.61; Cl, 23.55%. Found: C, 32.21; H, 4.69; N, 18.32; Cl, 23.34%.

EXAMPLE 22

(a) 1-(2,3,4-tri-O-acetyl-6-O-tosyl-β-D-glucopyranosyl)-3-methylurea

A suspension of 1-(β-D-glucopyranosyl)-3-methylurea (3.23 g, 13.7 mmol) in pyridine (50 ml) was mixed with a solution of tosyl chloride (3.12 g, 16.4 mmol) in pyridine (6 ml), and the mixture was stirred for 18.5 hours at 5° C under ice-cooling and then for further 43 hours at ambient temperature, followed by addition of a further volume of the solution of tosyl chloride (1.40 g, 7.3 mmol) in 3 ml of pyridine. The mixture was stirred for further 23 hours. Thin layer chromatography of the reaction mixture on silica gel using chloroform-methanol (2:1 by volume) as eluent gave no spot at Rf 0.43 which is of the starting compound, but a main spot at Rf 0.75.

The reaction mixture was poured into 800 ml of ice-water and stored overnight in cold. A syrupy phase deposited, and the upper aqueous layer was removed by decantation and concentrated to dryness under a reduced pressure. The residue was then subjected to acetylation by reacting with acetic anhydride in pyridine, thus affording 5.47 g of a syrup. This syrup was subjected to column chromatography with 100 g of silica gel and using benzene-isopropanol (10:1 by volume) as eluent. Such fractions of the eluate which gave a single spot at Rf 0.39 were combined together and concentrated to dryness by evaporating the solvent under a reduced pressure. Crystallization of the residue from n-propanol gave the titled compound. Yield 2.20 g (31.1%). mp. 118.5°–120° C. $[\alpha]_D^{20}$ +20.1° (c 2.45, chloroform).

(b) 1-(2,3,4-tri-O-acetyl-6-deoxy-6-iodo-β-D-glucopyranosyl)-3-methylurea

A solution of 2.38 g (4.6 mmol) of 1-(2,3,4-tri-O-acetyl-6-O-tosyl-β-D-glucopyranosyl)-3-methylurea in 15 ml of dioxane was admixed with 6.64 g (44.3 mmol) of sodium azide, and the admixture was stirred at 100° C for 3 hours and then cooled to ambient temperature. The reaction mixture was poured into a mixture of 100 ml of chloroform and 20 ml of water under stirring. The chloroform layer was washed with saturated aqueous solution of sodium chloride, with aqueous 20% sodium thiosulfate and then with water, followed by drying over anhydrous sodium sulfate. The chloroform layer so treated was then concentrated to dryness under a reduced pressure, leaving 3.90 g of an amorphous solid as the residue. This solid was subjected to column chromatography with 100 g of silica gel using benzene-n-propanol (10:1 by volume) as eluent. Such fractions of the eluate which gave a single spot at Rf 0.46 were combined together and concentrated to dryness by evaporating the solvent under a reduced pressure. The residue was taken up into a volume of methanol, followed by addition of 2-fold volume of water, so that the titled compound deposited as crystals. Yield 1.47 g (67.6%). mp. 144°–147° C $[\alpha]_D^{27}$ +2.4° (c 1.4, chloroform).

(c) 1-(2,3,4-tri-O-acetyl-6-deoxy-β-D-glucopyranosyl)-3-methylurea 1-(2,3,4-tri-O-acetyl-6-deoxy-6-iodo-β-D-glucopyranosyl)-3-methylurea (661 mg) was dissolved in 20 ml of ethyl acetate and subjected to catalytic hydrogenation for 2 hours in the presence of 7 ml of Amberlite IR-45 (OH$^-$ form) and in the presence of Raney nickel catalyst at ambient temperature at an initial hydrogen pressure of 3.4 kg/cm$^2$, thus converting the azido group into amino group.

Thin layer chromatography of the reaction mixture on silica gel using benzene-isopropanol (6:1 by volume) as eluent gave no spot at Rf 0.39 which is of the starting compound, but a single spot at Rf 0.32.

After the removal of the catalyst and the ion-exchange resin by filtration, the reaction mixture (namely, the filtrate) was concentrated to dryness under a reduced pressure. Recrystallization of the resulting crystalline residue from ethanol gave the titled compound. Yield 341 mg (70.3%). mp. 180°–182.5° C. $[\alpha]_D^{22}$ +22.4° (c 0.56, chloroform).

(d) 1-(6-deoxy-β-D-glycopyranosyl)-3-methylurea

A solution of 1.42 g of 1-(2,3,4-tri-0-acetyl-6-deoxy-β-D-glycopyranosyl)-3-methylurea in 6 ml of methanol was admixed with 1 ml of 1N sodium methoxide in methanol, and the admixture was allowed to stand for 22 hours at ambient temperature.

The reaction mixture was neutralized by addition of a cation-exchange resin, Amberlite IR-120 (H$^+$ form), freed from the resin by filtration and then concentrated to a syrupy residue by evaporating the solvent under a reduced pressure. Crystallization of the residue from ethanol gave the titled compound. Yield 0.66 g (73.1%). mp. 194°–196° C. $[\alpha]_D^{28}$ −23.9° (c 1.0, water).

(e) 1-(6-deoxy-β-D-glycopyranosyl)-3-methyl-3-nitrosourea 1-(6-deoxy-β-D-glycopyranosyl)-3-methylurea (617 mg, 2.8 mmol) and sodium nitrite (242 mg, 3.5 mmol) were dissolved in 4 ml of water, and to the resulting solution was added 0.5 ml of glacial acetic acid under ice-cooling and stirring. The mixture was stirred for 1 hour under ice-cooling and then stored overnight in a refrigerator to complete the nitrosation.

The reaction mixture was treated with Amberlite IR-120 (H⁺ form) for the removal of sodium cation and was then concentrated to dryness by evaporating the solvent under a reduced pressure. Digestion of the resulting crystalline residue with ethanol gave the titled nitroso compound. Yield 516 mg (71.3%). m.p. 76°–77° C (with decomposition). $[\alpha]_D^{27}$ −24.0° (c 1.1, water).

IR. spectrum (in KBr): 1745 (C=O, amide I), 1535 (CNH, amide II) and 1470 cm⁻¹ (N=O)

Elemental analysis: Calcd. for $C_8H_{15}N_3O_6 \cdot \frac{1}{2}H_2O$: C, 37.21; H, 6.25; N, 16.27%. Found: C, 36.94; H, 6.11; N, 16.66%.

EXAMPLE 23

(a)

1-(2-chloroethyl)-3-(6-deoxy-β-D-glycopyranosyl)urea

A solution of 234 mg (0.91 mmol) of 1(6-deoxy-β-D-glycopyranosyl)-3-methyl-3-nitrosourea in 2 ml of water was admixed with a solution of 401 mg (3.5 mmol) of 2-chloroethylamine hydrochloride and 0.5 ml (3.3 mmol) of triethylamine in 3 ml of aqueous 50% ethanol. The admixture was stirred for 2 hours at ambient temperature, and the reaction mixture was passed through a column (10 × 160 mm) of Amberlite IRA-400 (OH⁻ form), which was then washed with water. The effluent was concentrated to dryness under a reduced pressure, and the crystalline residue so obtained was subjected to chromatography in a column (8 × 350 mm) of silica gel (8 g) using chloroform-methanol (5:2 by volume) as eluent. Such fractions of the eluate which gave a single spot at Rf 0.50 were combined together and concentrated to dryness by evaporation of the solvent under a reduced pressure. Recrystallization of the residue from acetone gave the titled compound. Yield 98 mg (37.7%). mp. 130°–132° C $[\alpha]_D^{24}$ −25.5° (c 0.5, water).

(b)

1(2-chloroethyl)-3-(6-deoxy-β-D-glycopyranosyl)-1-nitrosourea

A solution of 193 mg (0.67 mmol) of 1(2-chloroethyl)-3-(6-deoxy-β-D-glycopyranosyl)urea in 1.5 ml of aqueous 99% formic acid was admixed with 99 mg of sodium nitrite under ice-cooling and stirring. The mixture was stirred for 3 hours under ice-cooling to complete the nitrosation. The reaction mixture was mixed with 0.5 ml of water and was then allowed to stand for 15 minutes, followed by the treatment with Amberlite IR-120 (H⁺ form) for the removal of sodium cation. The reaction mixture was subsequently concentrated to a syrupy residue by evaporation of the solvent under a reduced pressure. The syrup was subjected to chromatography in a column (8 × 300 mm) of silica gel (7 g) and using chloroform-methanol (4:1 by volume). Such fractions of the eluate which gave a single spot at Rf 0.58 were combined together and concentrated to dryness under a reduced pressure, affording 145 mg (72.3%) of the titled nitroso compound as a glassy but hygroscopic solid or pale yellow color. $[\alpha]_D^{26}$ −5.6° (c 0.8, water).

The above titled nitroso compound (75 mg) was acetylated by reacting with acetic anhydride in pyridine. The reaction mixture from the acetylation was concentrated to dryness under a reduced pressure, leaving a crystalline residue. Digestion of this residue with isopropanol gave 57 mg of 1-(2-chloroethyl)-3-(2,3,4-tri-O-acetyl-β-D-glycopyranosyl)-1-nitrosourea as crystals. Yield 53.4% mp. 143°–144° C.

EXAMPLE 24

Tetra-N-(N′-methyl-N′-nitroso)carbamoyl-ribostamycin

Tetra-N-(N′-methyl)carbamoyl-ribostamycin (1.0 g) was dissolved in 30 ml of ice-cooled water, and the resulting solution was admixed with 0.6 g of sodium nitrite. To the admixture so obtained which was in the form of a solution was added dropwise 2.0 ml of glacial acetic acid under ice-cooling and stirring. The mixture was constantly stirred for about 2 hours and then maintained at 0° C overnight to complete the nitrosation. The reaction solution was evaporated in vacuo below 25° C. The residue was taken up into a small volume of methanol, and the resulting methanolic solution was again evaporated to dryness. The residue so obtained was taken up into about 20 ml of anhydrous methanol and the small amount of insoluble matter was filtered off. The filtrate was concentrated to a volume of about one-fourth the original volume by evaporating the solvent under a reduced pressure.

The concentrated solution was cooled down to minus 20° C to deposit a pale yellow amorphous product. The crystals were removed by filtration, and the mother liquor was admixed with its 2-fold volume of ethyl ether, followed by cooling to deposit a further amount of an amorphous product. The product deposited were collected by filtration, affording 0.68 g of the titled compound as an amorphous and hygroscopic solid of pale yellow color. mp. 88° C (decomposition with foaming). $[\alpha]_D^{23}$ +35° (c 1.0, methanol).

Elemental analysis: Calcd. for $C_{25}H_{42}N_{12}O_{18}$: C, 37.59; H, 5.30; N, 21.05%. Found: C, 36.61; H, 5.40; N, 19.87%.

EXAMPLE 25

Tetra-N-[N′-(2-chloroethyl)-N′-nitroso]-carbamoyl-ribostamycin

Tetra-N-[N′-(2-chloroethyl)]carbamoyl-ribostamycin (1.9 g) was dissolved in 30 ml of cold water, and the resulting solution was admixed with the same volume (30 ml) of glacial acetic acid. To the admixture was gradually added 1.1 g of sodium nitrite under ice-cooling and stirring. The mixture so obtained was stirred for 2 hours under ice-cooling, to complete the nitrosation. The reaction mixture was treated with Amberlite IR-120 (H⁺ form) to remove sodium ion therefrom. The reaction mixture was then filtered and the filtrate was evaporated under a reduced pressure below 25° C. The residue was dissolved in ethanol, and the solution was again concentrated in the same manner as above. The residue so obtained was taken up into a small volume of ethanol, and to the resultant solution was added a small volume of ethyl ether so that the desired product precipitated. The precipitate was collected by filtration, washed with ethyl ether and then dried in a disiccator. There was obtained the title compound in a yield of 0.9 g. mp. 105° C (decomposition with foaming). $[\alpha]_D^{24}$ +30.7° (c 1.0, methanol).

What we claim is:

1. Nitrosourea of the formula:

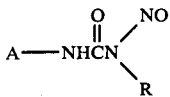

wherein A represents a glycosyl selected from the group consisting of maltosyl, glucosyl, mannosyl, galactosyl, xylosyl, and lactosyl and R represents a halo-substituted lower alkyl.

2. Nitrosourea as claimed in claim 1 wherein glucosyl is β-D-glucopyranosyl.

3. Nitrosourea as claimed in caim 1 wherein mannosyl is β-D-mannopyranosyl.

4. Nitrosourea as claimed in claim 1 wherein galactosyl is β-D-galactopyranosyl.

5. Nitrosourea as claimed in claim 1 wherein xylosyl is β-D-xylopyranosyl.

6. Nitrosourea as claimed in claim 1 wherein halosubstituted lower alkyl is chloroethyl.

7. Nitrosourea selected from:
1-(2-chloroethyl)-3-(β-D-glucopyranosyl)-1-nitrosourea;
1-(2-chloroethyl)-3-(β-D-mannopyranosyl)-1-nitrosourea;
1-(2-chloroethyl)-3-(β-D-galactopyranosyl)-1-nitrosourea;
1-(2-chloroethyl)-1-nitroso-3-(β-D-xylopyranosyl)urea;
1-(2-chloroethyl)-3-(β-D-maltosyl)-1-nitrosourea; and
1(2-chloroethyl)-3-(β-D-lactosyl)-1-nitrosourea.